United States Patent [19]

Barton et al.

[11] Patent Number: 5,601,814
[45] Date of Patent: Feb. 11, 1997

[54] USE OF IL-6 TO TREAT TOXIC SHOCK

[75] Inventors: Beverly Barton, West Orange; Jennifer Shortall, Flanders, both of N.J.

[73] Assignee: Schering Corporation, Kenilworth, N.J.

[21] Appl. No.: 286,315

[22] Filed: Aug. 5, 1994

[51] Int. Cl.$^6$ ................................................. A61K 45/05
[52] U.S. Cl. ...................... 424/85.2; 424/85.1
[58] Field of Search ................... 424/85.2, 85.1

[56] References Cited

U.S. PATENT DOCUMENTS

| | | | |
|---|---|---|---|
| 5,186,931 | 2/1993 | Kishimoto et al. | 424/85.2 |
| 5,271,931 | 2/1993 | Lotz et al. | 424/85.5 |
| 5,300,292 | 4/1994 | Ulich | 424/85.2 |
| 5,338,834 | 8/1994 | Williams | 530/351 |
| 5,437,863 | 8/1995 | Williams et al. | 424/85.1 |

FOREIGN PATENT DOCUMENTS

| | | |
|---|---|---|
| 5155779 | 6/1993 | Japan . |
| 05155779 | 6/1993 | Japan . |
| 93/11793 | 6/1993 | WIPO . |

OTHER PUBLICATIONS

Zhou et al., Endocrinology, vol. 133(6), pp. 2523 to 2530, 1993.
Starnes et al., J. Immunol. 145:4185 (1990).
Starnes et al., J. Immunol. 148:1968 (1992).
Wolff, New Engl. J. Med. 324:486 (1991).
Ziegler et al., New Engl. J. Med. 324:429 (1991).
Barry et al. JAMA (United States) Jan. 24, 1992, 39(6):856.
Marrack et al., J. Exp. Med. 171:455 (1990).
Miethke et al., Chem. Immunol. 55:172 (1992).
Miethke et al. J. Exp. Med. 175:91 (1992).
Resnick et al., 116:321 (1990).
Todd et al., Drugs (United States) 39(6):85 (1990).
Wright et al., Ann. Emerg. Med. (United States) 17(3):268 (1988).
Aderka et al., J. Immunol. 143:3517 (1989).
Barton et al., Infec. Immun. 61:1496 (1993).
Calandra et al., Diagn. Microbiol. Infec. Dis. 13:377 (1990).
Debets et al., Crit. Care Med. 17:489 (1989).
Franks et al., Infec. Immun. 59:2609 (1991).
Gadina et al., J. Exp. Med. 173:1305 (1991).
Bjork, et al., Endotoxin and *Staphylococcus aureus* Enterotoxin A Induce Different Patterns of Cytokines, Cytokine, vol. 4, No. 6 (Nov.), 1992: pp. 513–519.

*Primary Examiner*—Chhaya D. Sayala
*Attorney, Agent, or Firm*—James M. Gould

[57] ABSTRACT

Methods and compositions are provided for treating toxic shock in a mammal. The methods comprise administering to a mammal afflicted with or at high risk for developing toxic shock an effective amount of IL-6.

6 Claims, No Drawings

USE OF IL-6 TO TREAT TOXIC SHOCK

TECHNICAL FIELD

This invention relates to a method for treating or preventing toxic shock and similar diseases in a mammal by administering Interleukin-6.

BACKGROUND OF THE INVENTION

Toxic shock syndrome (TSS) is an acute febrile, exanthematous illness associated with multisystem failure including shock, renal failure, myocardial failure and adult respiratory distress syndrome (ARDS) (Todd et al., Drugs (United States) 39(6):856 (1990)). Symptoms of TSS include fever, pharyngitis, diarrhea, vomiting, mylagia, and a scarlet fever-like rash. TSS may progress rapidly (within hours) to signs of hypovolaemic hypotension such as orthostatic dizziness or fainting.

Patients with toxic shock syndrome usually have a staphylococcal infection such as a surgical wound infection or soft tissue abscess, or they may have TSS during menstruation associated with staphylococcal infection arising out of the use of a vaginal device such as tampons (Todd et al., supra).

*Staphylococcus aureus* and group A *Streptococcus pyogenes* are both known to produce toxic shock syndrome characterized by hypotension and multisystem organ failure (Barry et al., JAMA (United States) Jan. 24, 1992, 267(24):3315). Stappylococcus aureus is isolated in virtually all cases of both menstrual and non-menstrual TSS (Wright et at., Ann. Emerg. Med. (United States) 17(3):268 (1988)). In their original description of TSS, Todd et al., (Lancet 2:1116 (1978)) thought that the multisystem dysfunction in TSS was related to one or more new exotoxins. Schlievert et al. (*J. Infec. Dis.* 143:509 (1981)) and Bergdoll et al. (*Lancet* 1:1017 (1981)) independently discovered a toxin that they named pyrogenic exotoxin C and staphylococcal enterotoxin F, respectively. Further studies of these proteins found them to be identical, and in 1984 the term toxic shock syndrome toxin 1 (TSST-1) was adopted to describe the toxin (Wright et al., supra).

TSST-1 is a protein that has been found in 90% to 100% of women with menstrual TSS. TSST-1 also has been found to produce emesis and diarrhea in monkeys, fever in rabbits, and is an inducer of interleukin-1 synthesis. interleukin-1, an endogenous human pyrogen, produces fever and proliferation of lymphocytes (Ikejima et al., *J. Clin. Invest.* 73:1312 (1984)).

A patient with TSS will have a one- to four-day prosyndrome consisting of fever, nonrigorous chills, and mylagias, primarily involving the proximal limb, abdominal, lumbar, and cervical muscles. These muscles are frequently tender to the touch. Most patients also develop malaise, arthralagias, diarrhea or loose stools, emesis, headache, sore throat, and orthostatic dizziness. Another very common symptom of TSS is a brawny non-pitting edema of the face, eyelids, and extremities.

The dermatologic manifestations of TSS are well described (see e.g., Wright et al., supra) and are present in all cases. The classical rash is described as sunburn-like, blanching, nonpruritic, macular erythromderma. While the rash is usually diffuse, it may be localized to the trunk, extremities, or even to a small area in the inguinal or periheal region. The rash is usually present with the initial presentation of the patient and usually fades in about three days. Other cutaneous manifestations are occasionally noted and include a papulopustular rash, petechiae, bullae, and areas of cutaneous hyperaesthesia. Surviving patients develop desquamation, mostly involving the hands and feet, about five to twelve days after the initial rash has resolved. Patients may also have delayed transient patchy alopecia or fingernail loss. Mucous membranes and the conjunctiva are frequently noted to be hyperemic, and a "strawberry" tongue has been frequently described.

Hypotension or orthostatic changes in blood pressure are seen in all patients with TSS by definition. The hypotension is multifactorial and likely is due to a combination of gastrointestinal losses, third space effect, and vasodilatation. Sinus tachycardia is usually present, although other ECG changes, including premature ventricular contractions on exertion, aberrant beats of bundle origin, first-degree heart block, flattened T waves, and non-specific ST-T wave changes, have been described as well.

Evidence of renal dysfunction is a common finding in TSS, frequently manifested by an increase in blood urea nitrogen (BUN) and creatinine, and decreased urine output. Dialysis has been required for acute tubular necrosis, a pathologic finding often present at necropsy. Sterile pyuria also has been noted in the majority of cases.

Neurologic manifestations, the most common being headache, are present in almost all cases. Examination of the cerebrospinal fluid will usually reveal normal glucose and protein levels but an occasionally elevated white blood cell count. Nonfocal neurologic abnormalities such as disorientation, confusion, hallucinations, and agitation occur in most patients and generally resolve within several days. Fatal cases have been reported to show cerebral edema and nonspecific neuronal changes.

Nonspecific laboratory abnormalities are seen frequently. The hematocrit in most patients with TSS is normal or mildly decreased, usually with a normochromic, normocytic red cell pattern. The white blood count will usually be increased with a large percentage of immature neutrophils. An absolute lympocytopenia is often present and normalizes over the course of the illness. Mild thrombocytopenia is common, although usually not severe. Common findings on clinical chemistry studies include hypoalbuminemia, hypocalcemia, hypophosphatemia, and hypomagnesiumemia. Hypotensive patients frequently are noted to have a metabolic acidosis with an increased lactate level.

Despite increasing knowledge about toxic shock syndrome, this illness continues to be a serious threat. Thus, there is a critical need for a novel means for the treatment of toxic shock syndrome.

SUMMARY OF THE INVENTION

This invention provides a method for treating toxic shock in a mammal comprising administering an effective amount of IL-6 to a mammal afflicted with toxic shock. This invention also provides a method for preventing toxic shock in a mammal comprising administering an effective amount of L-6 to a mammal susceptible to or at high risk for developing toxic shock. A pharmaceutical composition for the treatment of toxic shock comprising IL-6 and a physiologically acceptable carrier, is also provided by this invention.

DESCRIPTION OF THE INVENTION

All references cited herein are hereby incorporated in their entirety by reference.

The term "toxic shock syndrome" as used herein is defined as a state of morbidity manifesting one or more of the following symptoms from the case definition listed below:

Fever: Temperature>38.9° C.

Rash: Diffuse macular erythroderma

Desquamation: 1 to 2 weeks after onset of illness, particularly of palms and soles Hypotension: Systolic blood pressure<90 mm Hg for adults or below fifth percentile by age for children below 16 years of age, orthostatic drop in diastolic blood pressure >15 HGg from lying to sitting, orthostatic syncope, or orthostatic dizziness Multisystem involvement (three or more of the following):

GI: Vomiting or diarrhea at onset of illness

Muscular: Severe myalgia or DPK level at least twice the upper limit of normal for laboratory Mucus membrane: Vaginal, oropharyngeal, or conjunctival hyperemia Renal: BUN or creatinine at least twice the upper limit of normal for laboratory or urinary sediment with pyuria (>5 leukocytes per high power field) in the absence of urinary tract infection Hepatic: Total bilirubin, SGOT, or SGPT at least twice the upper limit of normal for laboratory Hematologic: Platelets <100,000/mm$^3$ CNS: Disorientation or alterations in consciousness without focal neurologic signs when fever and hypotension are absent The symptoms listed above are illustrative of specific selection criteria to be used in determining candidates for the proposed method of treatment; the scope of the invention, however, is not to be considered strictly limited by values listed above, as they are merely suggested guidelines for the purposes of diagnosis. The effectiveness of treatment can be assessed by monitoring the above described manifestations of toxic shock.

IL-6 can be made by standard methods. For example, oligonucleotide probe mixtures based on known IL-6 nucleotide sequences can be used to identify DNA encoding IL-6 in genomic or cDNA libraries prepared by standard methods. (See, e.g., Maniatis et al., *Molecular Cloning: A Laboratory Manual*, 1982, Cold Spring Harbor Laboratory). DNA thus identified can be excised from the library by restriction endonuclease cleavage or prepared using appropriate primers and the polymerase chain reaction (PCR) method (Saiki et at., Science 239:487 (1988)), sequenced and expressed in a eukaryotic expression system or (following intron deletion by standard methods if necessary) in a prokaryotic or eukaryotic expression system. Of course, both cDNA and genomic DNA libraries can be screened by the application of standard expression cloning methods, instead of by the use of oligonucleotide probes or PCR. IL-6 thus produced is detected through the use of known immunochemical or bioassay methods.

Types of IL-6 derived from various species of origin, including human IL-6, are also commercially available, e.g., from Genzyme Corporation, Cambridge, Mass., and are generally supplied in a lyophilized form that can be reconstituted just prior to use in a pharmaceutically acceptable carrier such as phosphate buffered saline or any of the other well known carriers. Pharmaceutical compositions of the present invention can be injected directly into the bloodstream intravenously or via an IV drip solution such as Ringer's lactate. Parenteral preparations that can be used include sterile solutions or suspensions. These preparations can be prepared with conventional pharmaceutically acceptable excipients and additives such as stabilizers and carriers. The solutions to be administered may be reconstituted lyophilized powders which may additionally contain, e.g., preservatives, buffers and dispersants. Preferably, the compositions are administered by intravenous injection.

Various compositions that can be used in connection with the present invention are described e.g., in Gilman, et al. (eds.) (1990) *The Pharmacological Bases of Therapeutics*, 8th Ed., Pergamon Press; and *Remington's Pharmaceutical Sciences*, 17th ed. (1990), Mack Publishing Co., Easton, Penn. Methods for administration are discussed therein and below, e.g., for oral intravenous, intraperitoneal, or intramuscular administration, transdermal diffusion, and others.

Pharmaceutically acceptable carriers can include water, saline, buffers, and other compounds described, e.g., in *Merck Index*, Merck & Co., Rahway, N.J.

While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration.

The formulations may conveniently be prepared in unit dosage form and may be prepared by any methods well known in the art of pharmacy. See, e.g., Gilman, et al. (eds.) (1990) *The Pharmacological Bases of Therapeutics, supra;* and *Remington's Pharmaceutical Sciences, supra; Avis, et al.* (eds.) (1993) *Pharmaceutical Dosage Forms: Parenteral Medications* Dekker, New York; Lieberman, et al. (eds.) (1990) *Pharmaceutical Dosage Forms: Tablets*, Dekker, New York; and Lieberman, et al. (eds.) *Pharmaceutical Dosage Forms: Disperse Systems*, Dekker, New York. The therapy of this invention may be combined with or used in association with other chemotherapeutic or chemopreventive agents.

The IL-6 used will preferably be that of the mammalian species being treated (e.g., human recombinant IL-6 is preferred for treating human beings).

As used herein the terms "susceptible to" or "at high risk for " developing TSS most often include patients with clinical conditions such as surgical infections, soft tissue abscesses, influenza complications, nasal packing, postpartum infection, and the use of intravaginal devices such as tampons, contraceptive sponges, and diaphragms (See, e.g., Wright et al., Ann. Emerg. Med. (United States) 17:268 (1988); and Todd, Drugs (United States) 39:856 (1990)). In addition, occasional instances of TSS have been reported with the following conditions: bacterial tracheitis, staphylococcal empyema, fasciitis, osteomyelitis, peritonsillar abscess, septic abortion, bacteremia, and *Staphylococcus aureus* infection at insulin pump infusion sites in patients with diabetes (Resnick, J. Pediatr. 116:321 (1990)).

In accordance with the present invention, mammals that are in need of treatment for toxic shock as defined above are administered an effective amount of IL-6 to abate the abovedescribed symptoms. Preferably, a dose of from about 1 g g per kilogram of body weight to about 400 µg per kilogram of body weight is administered. More preferably, a dose of from about 2 µg per kilogram of body weight to about 200 µg per kilogram of body weight is administered.

Even more preferably, a dose of from about 2 μg to 120 μg per kilogram of body weight is administered. The precise amount of IL-6 to be administered would be determined by the attending clinicians, taking into account the etiology and severity of the disease, the patient's condition, sex, age, and other factors.

In the Example below, pre-treatment of mice with mouse IL-6 was done in order to facilitate adequate circulating concentrations in the bloodstream at the time of SEB-gal administration, because intraperitoneal injection of IL-6 requires a longer diffusion period to enter the bloodstream than other routes of administration (such as intravenous injection). Intraperitoneal injection was selected in this model due to the difficulty of intravenous injection in the mouse. The preferred route of administration would normally be intravenous injection, where bioavailability of the circulating therapeutic agent would be as rapid as 10 minutes. The actual timing of administration to a patient with or at risk for developing TSS, is not to be construed to be limited to the Example, however. Administration of IL-6 to an individual demonstrating symptoms of or at high risk for developing TSS can be before, during, or after the onset of any of the manifestations of clinical disease state as described above.

EXAMPLE

The present invention can be illustrated by the following Example, but this invention should not be construed as limited thereby.

MATERIALS

Male BALB/c mice (5–6 weeks) were obtained from Jackson Laboratories, Bar Harbor, Me. Endotoxin-free phosphate buffered saline (PBS) was purchased from GIBCO, Grand Island, N.Y. *Staphylococcus aureus* enterotoxin B (SEB) was purchased from Toxin Technology, Inc., Sarasota, Fla. D-galactosamine was obtained from Sigma Chemicals, St. Louis, Mo. Purified hamster gamma globulin (HGG), a protein control, was purchased from Organon Teknika, Durham, N.C. Mouse IL-6 was obtained from Biosource, Camarillo, Calif.

PROCEDURES

Enterotoxin B is a *S. aueus* product (SEB) known to cause toxic shock syndrome. D-galactosamine is a hepatotoxin shown to potentiate the lethal effects of SEB (Miethke et al. *J. Exp. Med.* 175:91 (1992)). The animal model used in these procedures, as described by Miethke et al. (*Chem. Immunol.* 55:172 (1992)) and Marrack et al. (*J. Exp. Med.* 171:455 (1990)), is considered predictive of clinical utility in mammals afflicted with toxic shock.

Groups of ten BALB/c mice were injected with mouse IL-6 one hour before injection of 25 μg SEB and 30 mg D-galactosamine. One control group was injected with PBS alone while another control group was injected with hamster gamma globulin (HGG). Animals were scored for mortality at 24 and 48 hours.

TABLE I

Effects of IL-6 on Mortality

| IL-6 (ng/mouse) | % dead (48 hr)[a] |
|---|---|
| 0 (PBS) | 100 |
| 0 (600 ng HGG) | 100 |
| 100 | 40* |
| 300 | 35* |
| 600 | 25* |

[a]The data are means of two separate experiments.
*P-value was 0.001 as determined by Fisher's Protected Least Significant Difference (PLSD) test. (See e.g., Snedecor and Corcoran, Statistical Methods, 7th Edition, 1980, Iowa State University Press).

RESULTS

As demonstrated above, IL-6 protected mice against mortality in the toxic shock model of Marrack et al., supra. Mortality in control groups treated with either PBS or HGG was 100%, whereas animals treated with IL-6 were conferred protection against lethality, ranging from 40% to 25%, depending on the dosage of IL-6 used.

Many modifications and variations of this invention can be made without departing from its spirit and scope, as will become apparent to those skilled in the art. The specific embodiments described herein are offered by way of example only, and the invention is not to be construed as being limited thereby.

What is claimed is:

1. A method for treating toxic shock in a mammal comprising administering an effective amount of IL-6 to a mammal afflicted with toxic shock.

2. The method of claim 1 in which the IL-6 is recombinant human IL-6.

3. The method of claim 2 in which the IL-6 is administered intravenously.

4. The method of claim 3 in which the amount of IL-6 is from about 1 μg/kg body weight per day to about 400 μg/kg body weight per day.

5. The method of claim 4 in which the amount of IL-6 is from about 2 μg/kg body weight per day to about 200 μg/kg body weight per day.

6. The method of claim 4 in which the amount of IL-6 is from about 2 μg/kg body weight per day to about 120 μg/kg body weight per day.

* * * * *